United States Patent [19]

Zarudiansky

[11] 4,414,984
[45] Nov. 15, 1983

[54] METHODS AND APPARATUS FOR RECORDING AND OR REPRODUCING TACTILE SENSATIONS

[76] Inventor: Alain Zarudiansky, 22 rue Exelmans, 78140 Velizy, France

[21] Appl. No.: 969,295

[22] Filed: Dec. 14, 1978

[30] Foreign Application Priority Data

Dec. 19, 1977 [FR] France ............................. 77 38181

[51] Int. Cl.³ .............................................. A61B 5/10
[52] U.S. Cl. ........................................ 128/774; 414/5
[58] Field of Search ................... 128/774, 739; 35/6, 35/12 E, 12 G, 17, 35 A; 340/407, 409; 414/5; 434/45

[56] References Cited

U.S. PATENT DOCUMENTS

| | | | |
|---|---|---|---|
| 2,972,140 | 2/1961 | Hirsch | 35/35 A |
| 3,097,436 | 7/1963 | Gaucher | 35/12 E |
| 3,171,549 | 3/1965 | Orloff | 340/407 |
| 3,309,795 | 3/1967 | Helmore | 35/12 E |
| 3,535,711 | 10/1970 | Fick | 414/5 |
| 3,736,363 | 5/1973 | Baessler et al. | 35/17 |
| 3,742,935 | 7/1973 | Baessler et al. | 35/17 |
| 3,818,487 | 6/1974 | Brody et al. | 340/407 |
| 3,831,296 | 8/1974 | Hagle | 35/35 A |
| 3,919,691 | 11/1975 | Noll | 340/407 |
| 3,954,101 | 5/1976 | Wachspress | 128/24 A |
| 4,119,212 | 10/1978 | Flemming | 414/5 |

OTHER PUBLICATIONS

Bejczy, A., "Effect of Hand-Based Sensors on Manipulator Control Performance", Mechanism & Machine Theory, vol. 12, #5, 1977, pp. 547-567.

Primary Examiner—Kyle L. Howell
Assistant Examiner—Francis J. Jaworski

[57] ABSTRACT

Apparatus for recording tactile sensations comprises a sensing or "receptor" glove used to effect a tactile exploration of an object whose "feel" is to be recorded. The glove typically includes a mosaic of pressure and temperature sensors in an "artificial skin", which is applied to the object during the tactile exploration, and is connected to further sensors for sensing the motivity parameters of the movable parts, e.g. fingers and wrist, during the exploration. The pressure and temperature sensors are preferably formed by localized diffusions of electrically conductive material into a sheet of a flexible insulating material. The electrical signals produced by the sensors are recorded, and are then used, with or without further processing, to operate apparatus for reproducing tactile sensations. This latter apparatus can comprise a motor glove for reproducing the motivity parameters, and/or a flexible membrane containing a mosaic of piston members and electrical heating elements for reproducing pressure and temperature sensations respectively.

5 Claims, 7 Drawing Figures

METHODS AND APPARATUS FOR RECORDING AND OR REPRODUCING TACTILE SENSATIONS

The present invention relates to the study, recording, creation and exploitation of sensations having tactile sensations as their origin or result.

It is known that the sense of touch results from sensitization by direct contact of certain localised specific centres of the skin (Meissner, Pacini, Frause and Ruffini tactile corpuscles, and free nerve endings). Certain tactile connections exist between the localised centres of the skin and certain muscular indicator elements for moving the muscles acted upon in the act of touching.

In studies of prostheses, it has been possible to make an artificial skin structure based on elementary electrodes disposed on each side of a flexible membrane. This artificial skin provides two types of information (signals proportional to pressure and information on sliding) usable in an implementation of an automatic prosthetic hand capable of ensuring initial gripping of an object and a final grip which prevents slipping of the object being held.

An object of the present invention is to provide a method and an apparatus permitting tactile sensations to be analysed, put in a memory, recreated or reproduced intact or modified according to the wishes of the user, and also to create synthetic tactile sensations without direct relationship with those to which man has so far been accustomed by his contact with the outside world.

The present invention provides a method of creating tactile sensations, comprising the following successive steps:
  spatially and temporally feeling (or probing) an object and detemining for each point of the object a value or a series of values of elementary factors capable of creating tactile sensations, such as position in space, point or mean pressure, temperature, etc;
  recording on a suitable support the measured values of the elementary factors, in the form of spatio-temporal sequences; and
  applying to a part of the human body an emitter of tactile sensations comprising excitation devices supplied with signals provided by the recording of said spatio-temporal sequences.

The present invention also provides an apparatus for performing this method, as well as the application of this apparatus and this method to the synthesis of tactile sensations characteristic of virtual objects different from real objects, either felt or feelable.

Other objects and characteristics of the invention will become apparent in the course of the detailed description hereinafter, which refers solely by way of non-limitative example to the attached drawings, in which.

Figure 1:
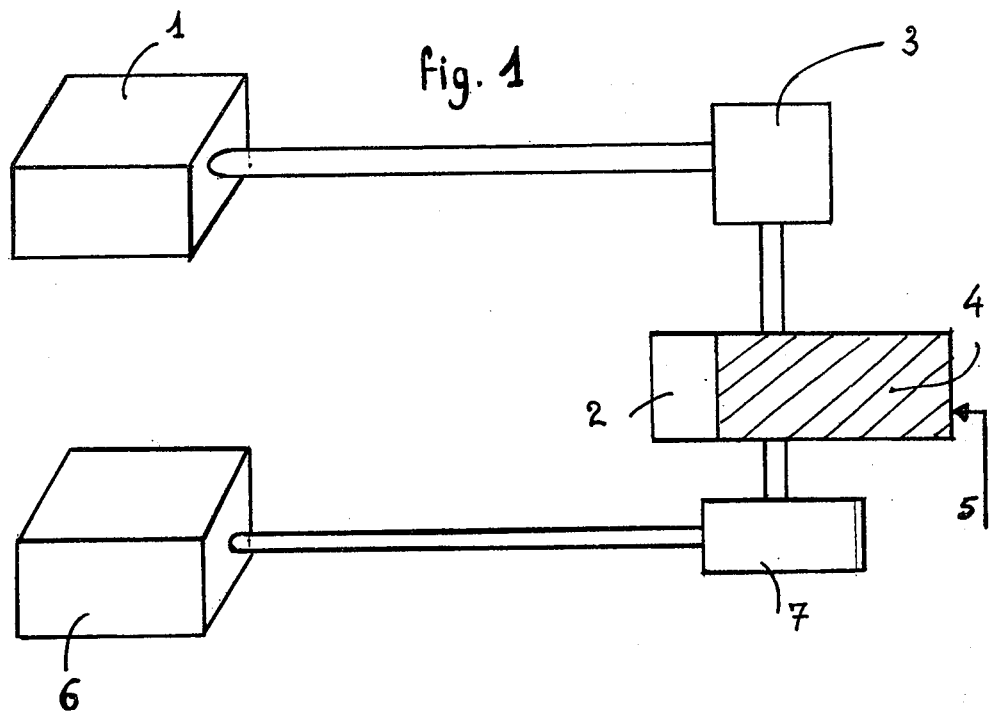
FIG. 1 shows in a schematic and symbolic manner a device according to the invention.

The apparatus according to the invention essentially comprises an element 1, which will be designated hereinafter by the term "receptor element", connected to the input of a "memory element" 2 by the intermediary of a data processing channel. This data processing channel can for example comprise transducer elements 3, a system 4 called a sequencer, and a control system 5.

The apparatus according to the invention additionally comprises an element 6, which will be designated hereinafter by the term "emitter", of which the input is connected to the output of the sequencer system 4 by the intermediary of transducer elements 7.

The operation of the apparatus according to the invention will become readily apparent after the explanation describing in detail the constitution and the operation of the elements which make up the apparatus.

Figure 2:
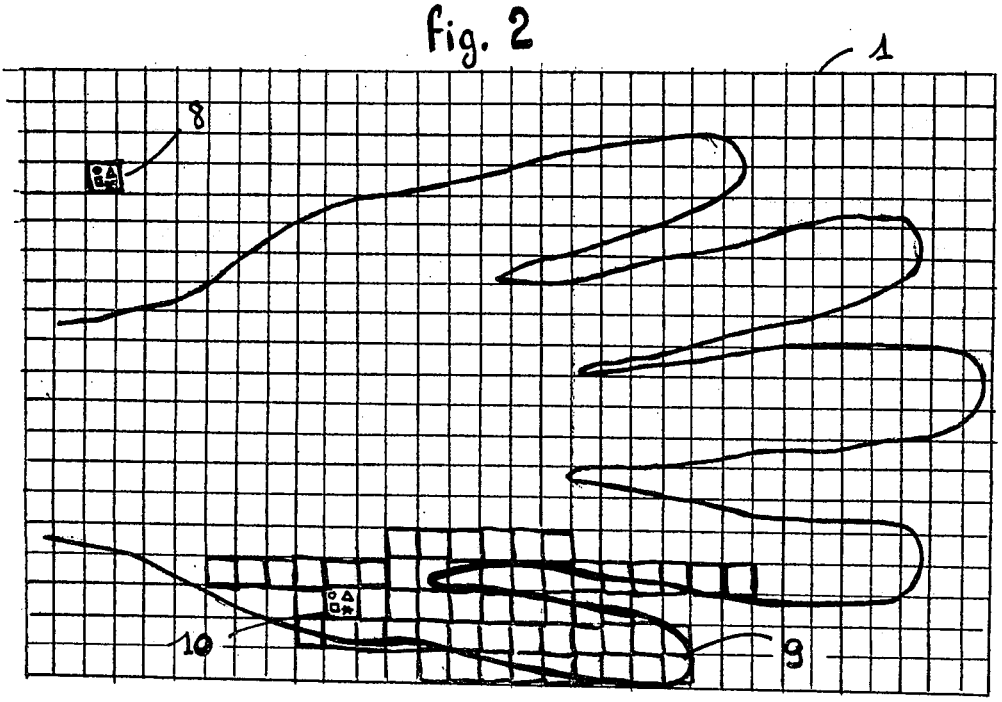
FIGS. 2 and 3 show schematically two embodiments of the receptor element forming part of the device illustrated in FIG. 1.

The receptor element shown in FIG. 2 is a device formed by a matrix of basic sensors such as those shown schematically at 8, 9 and 10. Each of these sensors is itself composed of elementary sensors represented schematically in the drawing, in the case corresponding to the sensor 8, by a circle, a triangle, a square and a star.

Each of the basic sensors can comprise any number of elementary sensors: each of these elementary sensors is a sensor capable of providing a signal representative of a parameter relevant to the sense of touch. By way of non-limitative example, the elementary sensors can be sensors of temperature, displacement or pressure. A basic sensor can be implemented in the form of a combination formed by a temperature sensor disposed on a rod movable perpendicularly to the plane of the matrix, the displacement of the rod being detected by a displacement sensor, and this rod additionally transmitting to a pressure sensor the force which is being applied to it.

Of course the elementary sensors and the basic sensors thus formed can be of any type, the signal representative of the parameter detected being an electric, light or magnetic signal, etc.

The number of basic sensors forming the receptor element can be different according to the dimensions of these sensors and the topology of the portion of the surface of the receptor that is desired to be rendered "sensitive". In other words, one or several basic sensors can be disposedin each of the squares shown in FIG. 2, or in certain of these squares only. For example, only the squares which would be covered by a hand placed on the receptor 1 can be provided with sensors.

Also, each of the squares can be provided with a sensor, but only certain of these sensors, for example those which would be covered by a hand placed on the receptor, need be sensitised.

The elementary pressure sensors can also be used as sensors of the presence of an object placed upon the receptor, the absence of action on this elementary pressure sensor putting out of circuit the elementary sensors of the basic sensor concerned.

From the description above, the operation of the receptor element 1 when this element 1 is in contact with an object can easily be deduced: signals are produced corresponding to each point of the object in contact with the receptor and representative of a point tactile sensation which would be created if the receptor element 1 were a human organ of touch (for example a hand).

At the output of the receptor element 1, constituted by the bundle of conductors connected to the elementary sensors and grouped by basic sensors, groups of signals representative of the point tactile sensation at the level of each of the basic sensors are therefore obtained.

This bundle of conductors (whether they be electric, magnetic, light or fluidic conductors) is connected to a set of elements known in the data processing domain as conditioners or transducers, intended for shaping the signals, quantifying the information and presenting this information in a usable form, for example in binary form compatible with data processing means used in the apparatus according to the invention.

The data processing means comprises a memory of any suitable type, and a device designated herein by the term multiplexer or sequencer, of a type known in itself, of which the function is to scan the signals provided by the sensors in order to store them in the form of sequential spatio-temporal recordings.

The multiplexer or sequencer device comprises programming and control means for selecting the elementary data to be put in storage, and perhaps for effecting processing of this data prior to its being put in storage. By way of example, the control device will be capable of taking account only of sensors topologically distributed in a manner comparable to a human hand, inhibiting the elementary sensors other than the displacement and pressure sensors, grouping the data relative to each point and recording in the principal memory only the data which have varied within certain limits between two measurement sequences, all in order to effect a recording of dynamic tactile sensations of the sliding type.

Thus, the assembly formed by the receptor 1, the transducers 3, the multiplexer 4 and its control device 5 permits sequential spatio-temporal recordings, derived from the sensors of the receptor during a tactile sequence where a real object has acted upon the sensors of the receptor, to be effected in the memory.

The emitter 6 is intended for reproducing on a human organ of touch, for example a hand, the sequence of variations of physical tactile parameters recorded in the memory by the receptor during a sequence of tactile exploration of the object.

This emitter can be constituted in different ways.

A first way consists of reproducing topologically the matrix of the receptor, but where each sensor element was, replacing it in the emitter with a corresponding excitation element. In place of a pressure sensor, a point pressure generator will be found, the same for the thermal element, the same for displacement and for each other required physical parameter. For the example under consideration, each of these excitation elements acted upon during the reproduction sequence will be suitable for applying to the human hand applied to the emitter the required excitation, in duration, variation and amplitude, corresponding to the spatio-temporal recording memorised.

Figure 3:
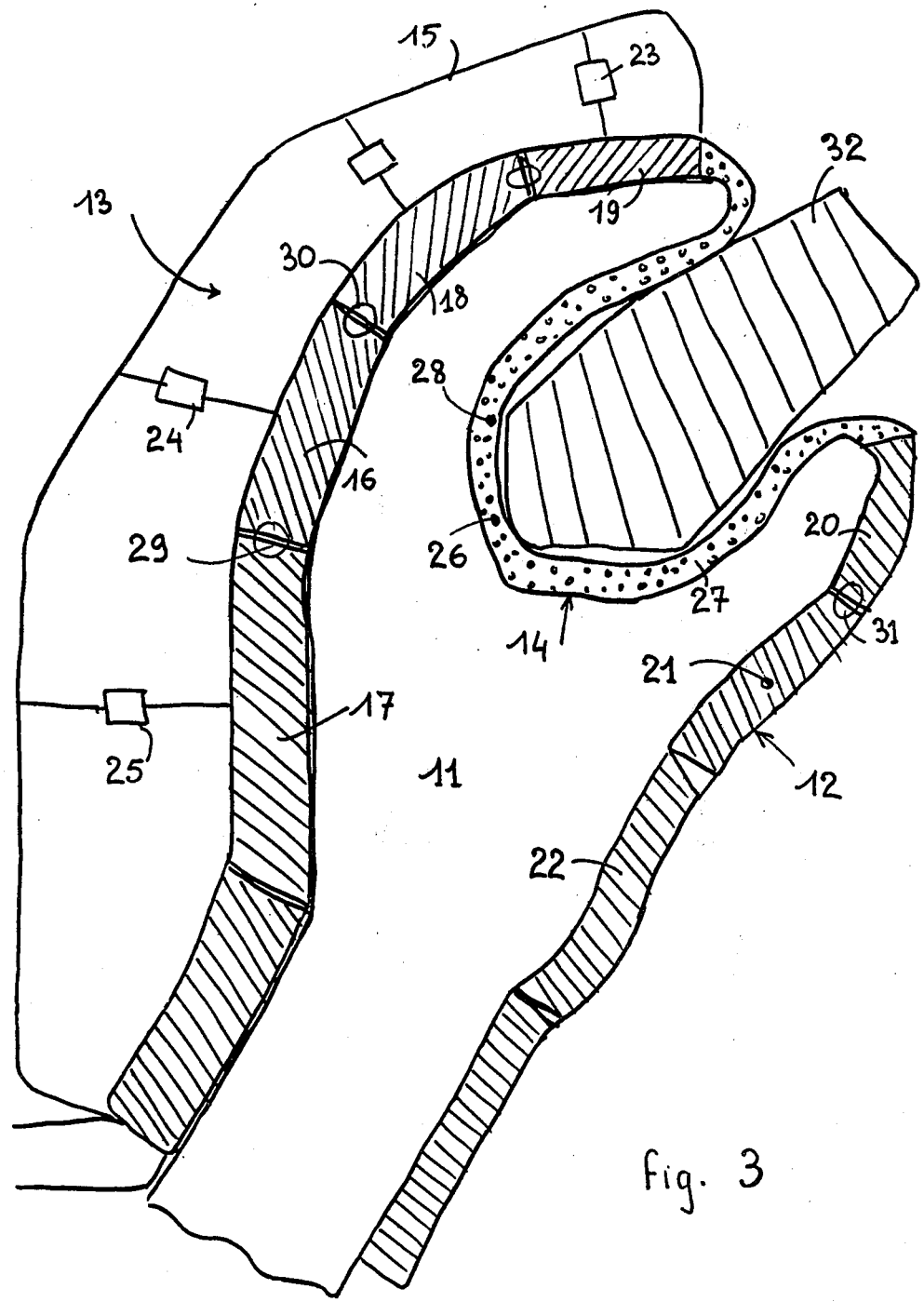

FIG. 3 shows another embodiment of a receptor element of the type shown schematically at 1 in FIG. 1.

This receptor can be implemented in the form of a kind of glove comprising an interior volume 11 intended for example to receive a hand. The envelope intended to receive the hand is formed by a wall capable of having two distinct parts. A first part corresponds to the external surface of the glove, generally designated in FIG. 3 by the references 12 and 13. This part of the envelope comprises sensor elements disposed and operated so as to provide data on the position in space of the fingers of the hand. By way of example, this part of the envelope can be constituted by articulated elements 16, 17, 18, 19, 20, 21, 22. Each of these elements can be connected to a rigid or semi-rigid shell or externalenvelope 15 by positional or displacement sensors, shown symbolically by the elements such as 23, 24, and 25. The data given by these sensors 23, 24 and 25 permit the position in space of each finger-joint or portion of the hand to be defined, the total of this data defining as a result the shape of the external volume of an object 32 as "seen" by the fingers of the hand. These data on the object 32 are complemented by data given by sensors such as those shown schematically at 26, 27, 28. These sensors 26, 27, 28 are disposed in the volume of the part 14 of the envelope of the glove, this part 14 corresponding to the internal surface of the hand in contact with an object 32.

The sensors 26, 27, 28 are, for example, pressure and temperature sensors distributed in the part 14 of the glove. This portion 14, as elsewhere the surface being susceptible of other implementations of the receptor such as those described above with reference to FIGS. 1 and 2, can be implemented for example in the form of an "artificial skin", such as is described in more detail with reference to FIG. 5.

According to another possible variant, the "exterior" portion 12, 13 of the glove comprises types of sensors shown schematically at 29, 30, 31 and measures the angle between the elements such as 16, 17, 18. This sensor system defines the angular position of each part of the hand or the fingers, and by that, the external shape of the object 32.

Of course, all the elements and structures relating to the receptor, such as are described above, can be transposed to the emitter, each of the sensors being replaced by an "excitation element" capable of reconstituting the position, angle, pressure or temperature, so as to make the human hand "feel the recorded object" by restoring its attitude with respect to the emitter—at its contact or at a distance. Of course the reference to a hand is made only by way of example, the receptors and emitters described being capable of being adapted to any other part of the body capable of the sense of touch.

Thus tactile sensations can be obtained at the level of the emitter, which according to circumstance are sensations received by the receptor or even created from a bank of elementary tactile sensations kept in memory and suitably processed by the programmable data processing apparatus described with reference to the elements 2, 4 and 5 of FIG. 1.

The apparatus according to the invention is particularly distinguished by the fact that the recorded tactile sensations can take account, not only of static parameters, but also of dynamic factors.

Thus the object to be tactilely recorded can be analysed by a receptor formed by a planar matrix of movable buttons in the course of a movement which would be imposed on the object, for example a rotational movement about a determined axis. The parameters of the rotation (phase, frequency, angular position from the origin) would be recorded in synchronism with the physical tactile data.

Having thus described the apparatus according to the invention, the structure of the elements of this apparatus, the examples of practical implementation of these elements and the operation of the whole assembly, it is now convenient to summarise the characteristic applications of the invention.

Just as described above, the known attempts to create an "artificial hand" or an "artificial skin" have all had as their object either to make prostheses, or to study certain parameters of the human or animal body for medical or paramedical purposes or even with the object of creating machines in the scientific field sometimes referred to as "robotics". According to the present invention, the receptor, which has the form of a generally flat-shaped sensing element, either in the form of a hand or a glove, essentially has the function of producing information about the volume, shape, topology, temperature or any other characteristic parameter of an object "seen" from the viewpoint of tactile sensations.

The data processing apparatus associated with the receptor essentially has as its function:
(a) the selection of certain data from the totality of the data available at the output of the receptor, this selection being capable of being effected
   either by a particular spatial or temporal scanning
   or by the sensitisation or inhibition of certain sensors. This selection can be effected, before recording, in a basic memory, or from the totality of the data recorded in this basic memory.
(b) the recording of sequences, in the basic memory or in secondary memories, the sequences being capable of being defined at will by the user as a function of the desired applications.
(c) the reproduction of these sequences for the attention of the emitter.

The emitter device has for its essential function to render capable of being sensed (or felt), at its level, the tactile sensations transmitted, with or without modification, by the data processing apparatus or created by this data processing apparatus either arbitrarily or according to determined and programmable laws from basic data which have been stored. The most simple and obvious application of the apparatus according to the invention consists of transmitting over a distance tactile sensations of an object for which it is known to transmit, by another route, other characteristics (for example, the image). However, this application is not, in fact, a simple transmission, for, in particular in the case of a receptor of the "glove" type described hereinbefore, the information transmitted includes a part which one could call subjective, to the extent that is depends on the operator and the way in which the operator takes up the object, in particular in the case when working not only with static feeling and holding but in dynamic conditions.

In the case of emitters and receptors in, for example, the form of gloves, the data analysed and transmitted comprises data on the three-dimensional configuration of the feeler glove and data on the tactile sensations created by feeling with this three-dimensional structure.

Study of the physiology of the senses has provided evidence that tactile sensations in fact include three groups of stimuli.

Group I Basic physical stimuli such as pressure, temperature, pain, transversal forces, etc.

Group II Auxiliary physical stimuli, issuing essentially from the hairy zones of the hand, or more exactly from the sense centres associated with the hairs of the external surface of the hand, sensitive to certain factors such as vibrations and the orientation of the hairs.

Group III Nervous stimuli associated with other elements of the hand, in particular to the articulation of the fingers and the wrist.

The data relating to these three groups of stimuli are transmitted to the central nervous system, which performs a synthesis of which the global result is the tactile sensation felt by the subject during the gripping and the static or dynamic feeling of an object.

The method and apparatus described above permit the recording, the processing and the reproduction of basic physical stimuli (group I) while taking account of the spatial and temporal positioning of the parameters sensed.

As it appears impractical to readily sense the stimuli of groups II and III with a view to reproduction, the present invention proposes to aleviate this drawback by proceeding to the recordal of factors outside the parameters of groups II and III, and by stimulating the reproduction of these parameters "in situ" in the nervous system of the subject. This is effected by action on the elements of the subject (fingers, finger-joints, wrist), of which the sense centres concerned simultaneously play the role of sensors and excitation elements.

It has been noted, in effect, that the stimuli of groups II and III are closely allied with external parameters known as "motivity" parameters, such as the position and movement of movable elements of the fingers and wrist. Thus if instead of the parameters of groups II and III, the motivity parameters are recorded, and if the hand of a subject is made to take the same positions and movements as those of a real tactile feeling, the subject will then feel the stimuli of groups II and III as if he were effecting a real tactile feeling. It is convenient to note in particular that the stimuli of group II, related to the hairs of the hand during a tactile feeling which does not put the hairs in direct contact with the object, are produced at least partly by the tension of the skin on the external surface of the hand, this tension being itself allied to the motivity parameters.

According to a modification of the present invention, the method of recording and reproducing tactile sensations relative to the tactile sensations relative to the tactile exploration of an object comprises the following operations:
(a) recording motivity parameters (movements and positions of the movable elements of the hand) during a sequence of real tactile exploration of an object;
(b) the reproduction and application to the movable elements of a hand of the motivity parameters with simultaneous recording of basic physical stimuli (pressure, temperature, etc.), all effected in contact with the object;
(c) the reproduction and application to the human hand of tactile sensations by the execution of a fictional tactile exploration comprising the reproduction of the motivity parameters combined with the reproduction of the basic physical stimuli.

The implementation of this modification of the method requires the use of "receptor" gloves and "emitter" gloves having the following functions, either separately or in combination:

A motivity receptor glove, adapted to fit a human hand and capable of recording motivity parameters relating to movements and positions of the human hand as the hand effects a real tactile exploration to find tactile sensations.

- A motor glove adapted to the human hand and capable of impressing or exercising on this hand a physical action tending to reproduce the aforementioned movements and positions either in the form of a forced action or a guiding action.
- A sensor glove for basic physical stimuli adapted to fit on the hand being moved or guided by the motor glove.
- An excitation glove, capable of reproducing and applying to the human hand the basic physical stimuli while it is being moved or guided by the motor glove.

Of course, the implementation of the method can be effected by complex gloves grouping several of the preceding functions.

It is appropriate to note particularly that the recording of motivity factors can be effected either by a glove proper, or by exterior means, for example by an optical or electromagnetic detector not physically connected to the hand making the first, real tactile exploration: for example, the analysis of the data provided by a television camera filming the tactile exploration permits the recording of the spatio-temporal data required for operating a motor glove which would reproduce the positions and movements of the real hand.

Operations (a) and (b) defined above can be effected simultaneously. According to a preferred embodiment of the invention, these operations are effected separately, in order to take account of the fact that the first tactile exploration is preferably effected without interposing, between the hand and the object, sensors which risk disturbing the sequence of the tactile exploration, which must in fact be a spontaneous tactile search of which the intermediate steps are constantly corrected by reflex action issuing from the central nervous system to take account of the real instantaneous sensations actually perceived by the subject effecting the tactile exploration. Similarly, operation (b) can be effected with the aid of a glove fitted on an artificial hand (that is to say in the absence of the human hand). However, it is preferable to effect this operation with the human hand to the extent that the presence of the real hand in the sensor glove for stimuli permits the reconstitution of the basic physical stimuli in a better manner, and in particular the thermal exchanges between the hand and the object through the stimuli sensors.

The simultaneous reproduction by means of a motor-excitation glove of the recordings effected during operations (a) and (b) permits the subject to make a synthesis of the physical sensations created by the excitation elements for the parameters of group I (basic physical stimuli) with the nervous sensations comprising the stimuli of groups II and III provoked "in situ" by the movement and the successive positions imposed on the movable elements of the hand of the subject effecting this fictitious tactile exploration.

The subject thus obtains tactile sensations which are created artificially but are very similar to the physical sensations which would be perceived by direct tactile exploration.

Figure 4:
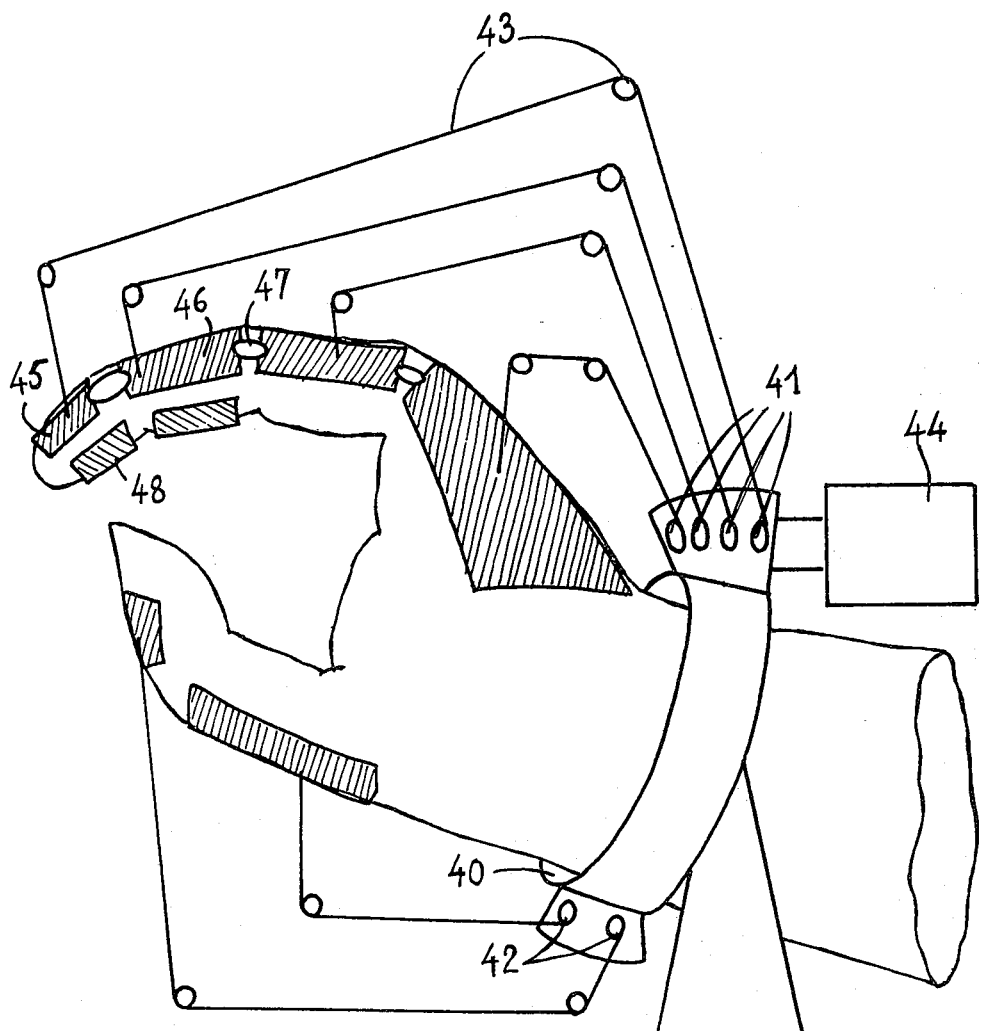
FIG. 4 shows schematically a human hand fitted with a glove according to the present invention, capable, according to the particular case, of being a "receptor" glove or an "emitter" glove for tactile sensations.

Of course, the recording of the different parameters can be modified to modify the sequences or to make any selections or additions, as described at the start of the present description, thus enlarging the spectrum of tactile sensations capable of being applied to the subject. The apparatus shown schematically in FIG. 4 comprises a bracelet 40 seving as a fixed reference on which the origin of a reference trihedral can be located.

To this bracelet is fixed an optical or mechanical apparatus permitting the positions of the elements of the hand in space and time to be determined. In the case of a mechanical implementation, this apparatus can be constituted by classical mechanical elements (rods, cables, pulleys, etc) represented schematically at 43 and connecting the movable elements of the hand to sensors 41-42 capable of producing signals representative of the position of the mechanical elements concerned and thus of the corresponding movable elements of the hand.

These signals are sent to data processing apparatus 44 (associated with the bracelet 40 or disposed at a distance) capable of recording the signals and processing them as described hereinbefore.

The glove described above is a receptor glove for motivity.

The motor glove can be analogously implemented, the sensor elements 41-42 being replaced by corresponding motor elements capable of acting on the elements 43 under the control of signals transmitted by the apparatus 44. The glove proper additionally comprises means for coupling the mechanical elements 43 to the movable elements of the hand. These means can for example be formed by plates or shells 45-46 fixed to the elements of the hand, either on its external surface or on the sides (in the case of the joints).

In a manner known per se, these shells can be connected to each other by articulations 47 or fixed on the surface of a lightweight glove of fabric or other flexible material.

In the case where the receptor glove for motivity is combined with the receptor glove for basic physical stimuli, the stimuli sensors can be fixed to the movable elements of the hand in the form of shells 48 or of sensors distributed over an "artificial skin", fixed to the hand and possibly mechanically to the elements constituting the motivity receptor glove.

The excitation glove, capable of reproducing the basic physical stimuli, can be implemented analogous to the receptor glove for the same stimuli.

Figure 5:
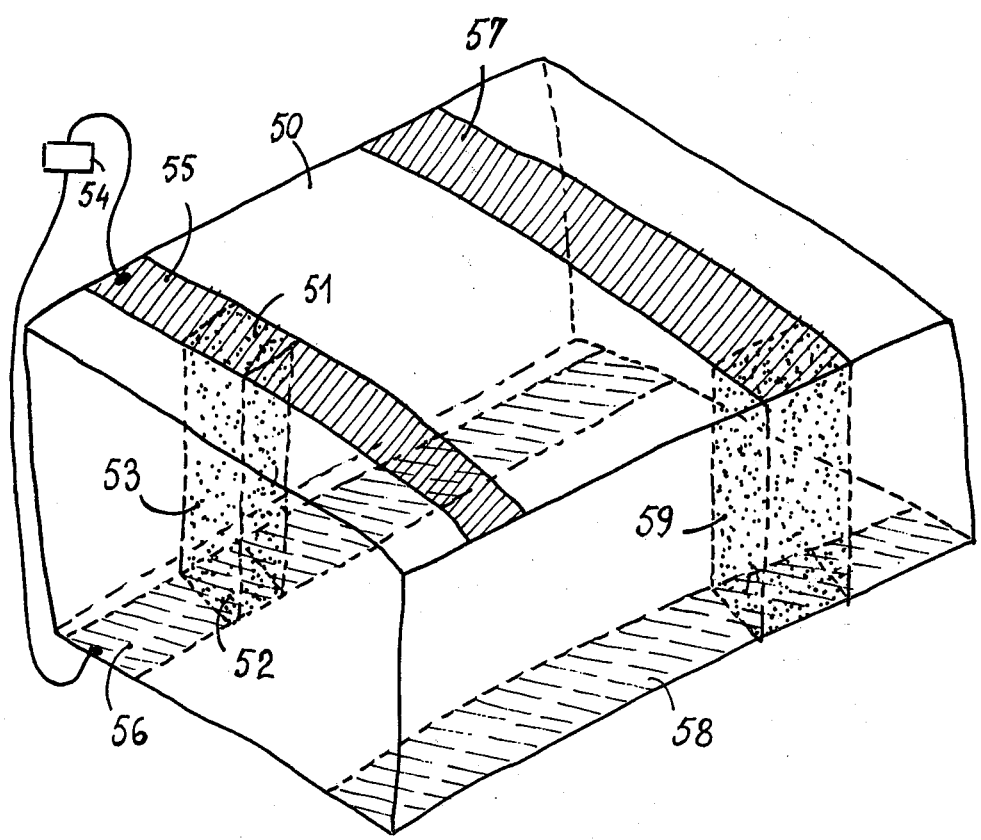
FIG. 5 shows schematically the structure of an "artificial skin" capable of being used for implementing a "receptor" according to the invention.

FIG. 5 shows schematically an advantageous embodiment of an "artificial skin", permitting the implementation of a sensor of the basic physical stimuli constituted by pressure and temperature. According to the present invention, a membrane 50 is used, the membrane being constituted by a flexible insulating material such as, for example, the synthetic materials known under the names "capton" and "silastene", or any material of the synthetic rubber type, capable of being doped (i.e. receiving a diffusion), by classical methods, with atoms, molecules or smaller or larger particles of electrically conductive materials. The diffusion of electrically conductive materials can be limited to certain portions of the volume of the material and can be of variable density according to the requirements. In particular, according to the present invention, certain portions of volume, such as the portion 53, include a diffusion such that the electrical resistance between the terminal surfaces 51 and 52 is a function of the force exerted on these surfaces 51 and 52. The element 51, 53, 52 thus constitutes a pressure sensor, variations of pressure being translated into variations of current flowing from a source of potential applied by means of electrodes 55 and 56, which are implemented for example by the deposition of metallic layers on the opposite surfaces of the material 50.

In other words, a matrix of pressure sensors can be obtained, disposed in the body of a layer of flexible material by suitably doping certain portions of this layer and by connecting the terminal parts of said portions to sources of potential.

In the same layer of flexible material 50, temperature sensors can also be implemented, for example in the form of thermocouples or thermistors, constituted by a first metal deposited on one of the faces of the material 50 (electrode 57), a second metal deposited on the other face of the material 50 (electrode 58) and a conductive connection obtained by a suitable diffusion of electrically conductive material, effected in the volume portion 59.

Thus it can be seen that judicious distribution of electrically conductive material in the zones such as 53 and 59, associated with the deposition of metallic electrodes such as 55, 56 57, 58 with a suitable choice of the metals used, permits a mosaic of sensors, some sensitive to pressure and others sensitive to temperature, to be obtained, the support of this mosaic being a flexible material capable of constituting an "artificial skin" suitable for use in apparatus according to the invention.

The thickness of such an artificial skin can, according to requirements, be of the order of a fraction of a micron or several hundred microns.

The implementation of an excitation glove capable of reproducing and applying physical stimuli to the skin, for example on the internal face (palm) of a hand, poses numerous problems.

The implementation of matrix elements comprising excitation elements operated by signals produced by a common type of energy can be envisaged. For example, by using electric energy, transducers of the piezoelectric type or magnetostrictive type for reproducing the effects of pressure, and transducers of the electrical resistance type or Peltier effect plate type for reproducing thermal effects, can be implemented. The constraints encountered are numerous:

the necessity of assembling a large number of excitation elements on a restricted surface: a few square millimeters for accommodating at least two or three types of sensors;

the necessity of moving the excitation elements in contact with the skin by of the order of one millimeter in order to produce maximum pressures on the skin;

the necessity of using pressure excitation elements having a good thermal conductivity in order to avoid disturbing thermal exchanges necessary to the reproduction.

As a result, it is particularly advantageous to create a type of excitation element which permits the combination in a single element or a single structure of excitation elements of different kinds, which assures, for example:

a relatively significant displacement with respect to the rest position;

a sufficiently large elementary force;

an effective active thermal transfer (cooling and heating).

Figure 6:
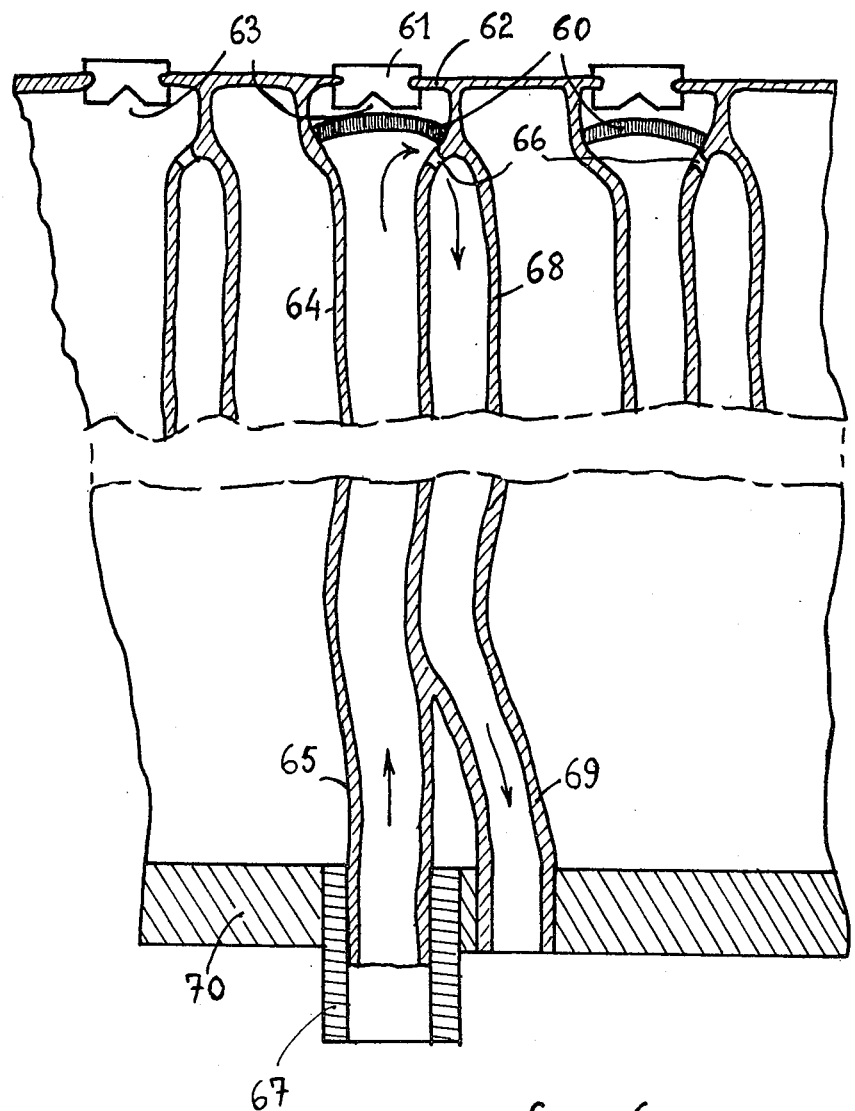
FIG. 6 shows schematically, in section, the fine structure of excitation elements.

FIG. 6 shows in schematic section the structure of an example of a practical implementation of a matrix excitation apparatus capable of reproducing on the skin the effects of pressure and temperature.

This structure comprises contact elements 61 formed for example by small pistons, of which the upper surface, intended for contact with the skin, can have an area of the order of a square millimeter. This piston is laterally located by a flexible membrane 62, for example of rubber, connected to other pistons of the same type, which thus form a mosaic of which the "cement" is flexible. The material constituting each of the elementary pistons must be a good thermal conductor. The lower face of the piston is in contact with a pressurised fluid serving on the one hand to supply or withdraw heat, and on the other hand to exert on the piston an upwardly directed force causing the piston to move a certain distance because of the elasticity of the membrane to which the piston is fixed. According to another modification, it is possible to let the piston, subject to a restoring element, slide substantially freely in a cylindrical housing provided in the wall of the membrane. In order to ensure good thermal transfer between the skin and the pressurised fluid, the lower face of the piston can be grooved or hollowed as shown at 63. The pressurised fluid is led into a cavity formed by the lower surface of the piston 63 and by the walls of a tube 64 forming a capillary of which the cross-sectional area is of the order of a millimeter.

The material forming the tube 64 must be a good thermal insulator and must have sufficient flexibility for the tube to be able to curve or bend easily when the pressure of the skin exerted on the assembly of the mosaic produces a significant depression in the mosaic.

The lower extremity 65 of the tube is connected to a pressurised fluid conduit 67.

The upper part of the tube 64 comprises a calibrated orifice 66 opening into a second capillary tube 68 of which the lower part 69 is vented to atmosphere. The combination of the orifice 66 and the tube 68 provides a pressure drop for the flow of the fluid greater than that of the tube 64, which permits the recovery at the level of the piston 61 of the greater part of the pressure applied to the tube 64 via its inlet conduit 67. The capillary tube 64 additionally comprises in its upper part, near the piston, a heater element formed for example by an electric resistance 60 connected by a conductor (not shown in the Figure) to a current source.

The structure described above thus generally comprises a flexible upper surface, formed by the mosaic of pistons 61 connected by the membrane 62, a bundle of capillaries 64 and 68 of which the upper ends are fixed to the membrane 62 at the periphery of the pistons 61 and a lower wall 70 (which can be rigid) and comprising apertures receiving the lower ends of the capillaries.

The volume contained between the upper surface (61-62) and the lower surface (70) is connected to a source of fluid whose pressure is in principle just sufficient to permit the membrane 62 to support the weight of the pistons 61 and the capillaries 64 and 68 in a floating state, without significant deformation in the rest position.

The structure of the excitation-material apparatus described above operates in the following manner. A cold fluid coupled to a pressure source is supplied via the conduit 67. It establishes in the capillary a constant fluid flow determined by the pressure drops due to the calibrated orifice 66 and the capillary 68. The pressure on the piston 61 is thus determined, and the piston pushed upwardly and exerts on the skin, placed on its exterior surface, a pressure of which the magnitude is a function of the fluid pressure at the inlet 67.

Because of the good thermal conductivity of the piston 61, a thermal exchange takes place between the skin and the piston and produces on the skin a temperature effect. The value of this temperature is adjusted according to requirements by operating the heating element 60, which raises the temperature of the fluid to the desired value.

It can therefore be seen that an excitation of the skin is obtained by the intermediary of the piston, which exerts at the same time a pressure effect and a temperature effect according to the value of the pressure of the fluid supplied at the inlet conduit 67 and the value of the electric current applied to the heating element 60.

Figure 7:
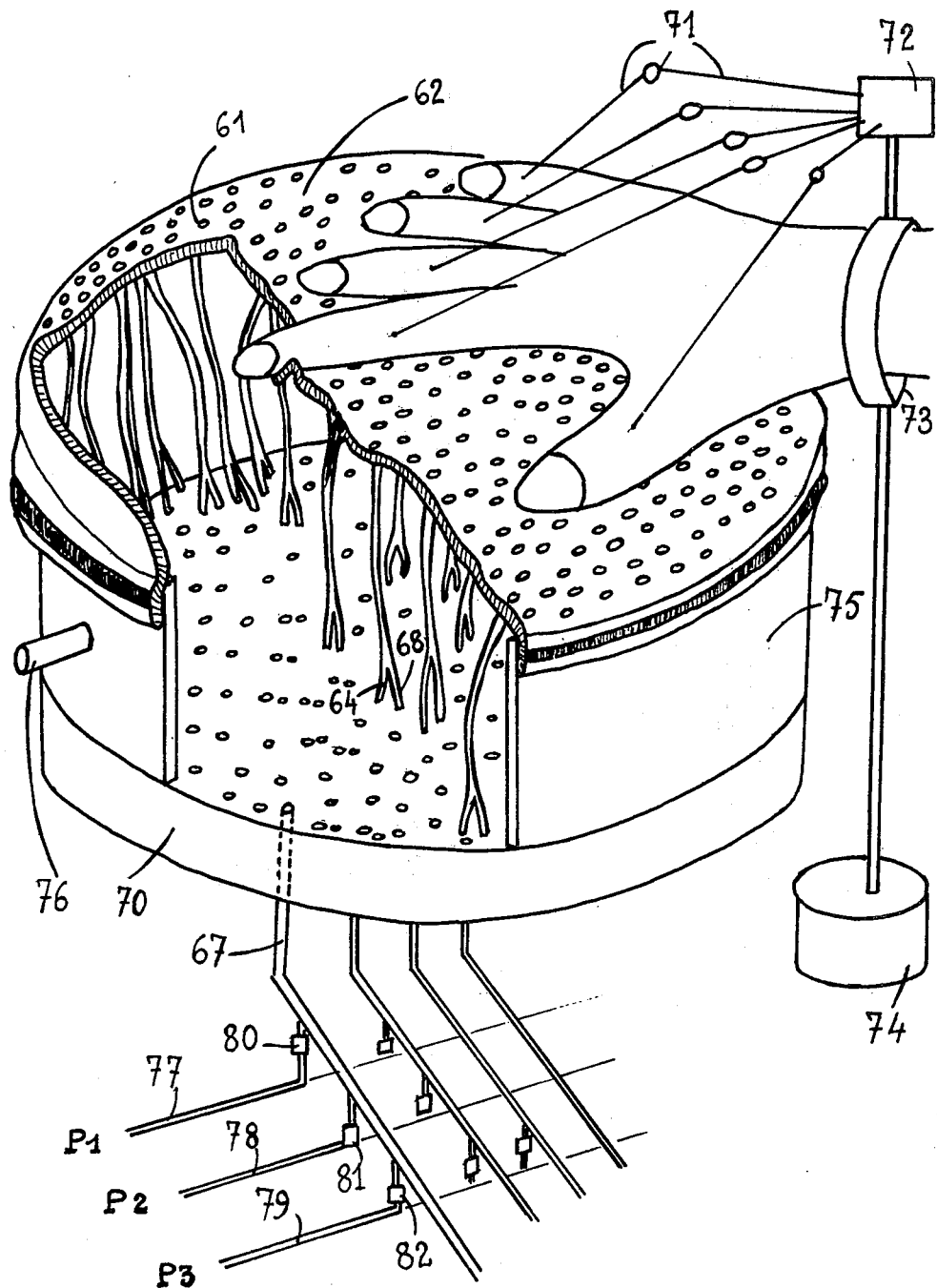
FIG. 7 illustrates schematically an excitation apparatus making use of the elements shown in FIG. 6.

FIG. 7 shows schematically an excitation assembly putting into effect the structure illustrated in FIG. 6.

The hand is supported by a motor glove comprising articulated elements 71 controlled by actuators 72, which are connected to a bracelet 73 fixed to a support 74. The inner face of the hand is applied to an excitation device formed by the pistons 61 disposed in the membrane 62. The surface 61-62 is supported around its periphery by a wall 75 forming with the lower surface 70 a cavity supplied with pressurised fluid by a conduit 76.

Each of the pistons 61 is connected by the capillaries 64-65 to tubes 67 supplying a suitable cold pressurised fluid, and by the capillaries 68 to atmosphere.

Each of the tubes 67 is connected to tubes such as 77, 78, 79 by the intermediary of electrically operable valves 80, 81, 82 or other controllable devices capable, on receipt of determined control signals, of connecting the tube 67 to sources of different pressures P1, P2, P3, Pn . . . .

Additionally, electrical conductors (not shown) connect the heating elements associated with the pistons to a matrix of contacts supplying to the heating elements requisite values of electric current.

It can be seen that the assembly described with reference to FIG. 7 permits the implementation of the method according to the invention so far as the simultaneous reproduction on a hand of the motivity factors and basic physical stimuli (pressure and temperature) factors is concerned.

Of course, the apparatus according to the invention permits not only the simple transmission of tactile sensations, but also their recording and transformation. By a judicious choice of the parameters sensed and reproduced, an apparatus applicable to the recognition of forms, in the widest sense of the term, is obtained; the factors recognised can be not only topological factors, but other characteristics such as, for example, temperature.

Thus the apparatus can be used for teaching purposes, to provide information about objects by touch, or for medical or paramedical purposes, for example the re-education or education of blind people or people having other infirmities capable of being compensated or helped by tactile sensations. In particular, one of the more significant applications results from the possibility of creating from the recording of tactile sensations transposed data, capable of appreciation by the sense of touch but completely different in their form and capable of being sensed or interpreted, for example, by a different part of the body from that which served as the base for the recording.

Besides the creation of standards of touch, embodiments of the apparatus permit stimulation of the local nervous system of the body with a view to producing curative, stimulating, euphoric or pleasant sensations, perhaps combined with sensations related to another sense (hearing, smell, sight . . . ).

The combination of different sensations, for example the coupling of vision and touch, permits the production of complex sensations for recreational purposes, as well as for psychological or medical purposes, which are all the more novel since the reproduced or synthetic tactile sensations need not correspond to the sensations to which man has become accustomed since birth by his contact with the outside world.

Finally, applications of a more utilitarian or industrial character should be mentioned, such as for example form (or shape) analysis as applied to the manufacture of objects. In this domain, the apparatus according to the invention can be applied to the production of objects intended to cover part of the human body (a shoe or a glove for example). In this case, the tactile sensations can be used for defining the object before it is made. For such an object must be characterised at each point, not only by its form, but also by the sensations it ought to create at the level of the organ of the body with which it will be in contact, for example by providing a flexibility or a resistance to pressure in accordance with stronger or weaker places.

What is claimed is:

1. A method of providing to a human subject tactile sensation simulating the tactile exploration of an object, comprising the steps of:

recording on a suitable support a first sequence of signals corresponding to spatial and temporal parameters, representative of a sequence of tactile exploration of a plurality of points of said object;

recording on a suitable support a second sequence of signals provided by sensing means operative to sensing, at least one parameter representative of tactile sensation given by each of said plurality of points of said object, said sensing means being operatively moved in contact with said object, so as to reproduce spatially and temporally, the above mentioned sequence of tactile exploration;

applying simultaneously to a part of the body of said human subject, transducer means respectively operative to impart movement to said part of the body in response to said recorded first sequence of signals to exert tactile stimuli to said part of the body in response to said recorded second sequence of signals.

2. A method according to claim 1, wherein said sequence of tactile exploration is carried out by the hand of a human operator, said hand being operatively connected with detecting means for the production of signals representative of the spatial and temporal parameters of, at least, one point of the hand of the human operator during the sequence of tactile exploration.

3. A method according to claim 1, wherein the recording of said second sequence of signals, is carried out during the movement of the hand of said human operator, said hand being equipped with a moving device, operative to impart to, at least, said one point of the hand, a movement repeating said sequence of tactile exploration in response to said recorded first sequence of signals, said moving device further comprising said sensing means connected to said at least one point of the human operator.

4. A method according to claim 1, wherein said recorded first and second sequences of signals are supplied to said transducer means, after having been submitted to controlled alteration by computer means, to modify and enlarge the spectrum of tactile sensations provided to the human subject.

5. A method according to claim 1, wherein said part of the body of the human subject is a hand.

* * * * *